United States Patent [19]

Alexander

[11] Patent Number: 4,818,977
[45] Date of Patent: Apr. 4, 1989

[54] COMBUSTIBLE GAS DETECTOR HAVING TEMPERATURE STABILIZATION CAPABILITY

[75] Inventor: William J. Alexander, Pittsburgh, Pa.

[73] Assignee: Mine Safety Appliances Company, Pittsburgh, Pa.

[21] Appl. No.: 116,163

[22] Filed: Nov. 3, 1987

[51] Int. Cl.⁴ .............................................. G08B 17/10
[52] U.S. Cl. ................................... 340/633; 73/27 R; 324/65 R
[58] Field of Search ....................... 340/633, 634, 632; 73/27 R, 23; 361/56, 57; 324/65 R, DIG. 1; 422/98, 96, 97; 307/362, 308; 338/34

[56] References Cited

U.S. PATENT DOCUMENTS

| | | | |
|---|---|---|---|
| 3,997,837 | 12/1976 | Betz et al. | 73/27 R |
| 4,028,057 | 6/1977 | Nelson | 340/633 |
| 4,080,821 | 3/1978 | Johnson | 73/27 R |
| 4,164,699 | 8/1979 | Timoshenko et al. | 340/634 |
| 4,305,724 | 12/1981 | Micko | 23/232 E |
| 4,533,520 | 8/1985 | Bossart et al. | 73/27 R |

Primary Examiner—Joseph A. Orsino, Jr.
Assistant Examiner—Jill D. Jackson

[57] ABSTRACT

A catalytic gas detector circuit in which the temperature of a resistance gas sensing element, contained in a bridge circuit, is reduced and therefore stabilized by energizing a transistor to draw off current from the sensing element when the sensing element is exposed to high concentrations of combustible hydrocarbon gases.

3 Claims, 1 Drawing Sheet

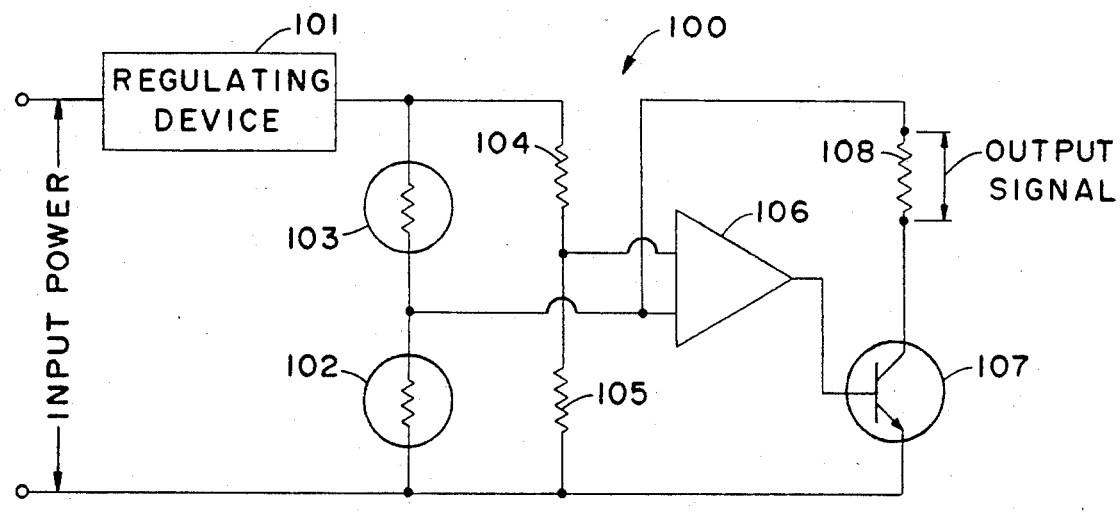

COMBUSTIBLE GAS DETECTOR HAVING TEMPERATURE STABILIZATION CAPABILITY

FIELD OF THE INVENTION

This invention relates to the field of combustible gas detectors having catalytic coated resistance sensing elements.

BACKGROUND OF THE INVENTION

Traditionally, combustible gas detectors used to detect the presence of combustible gases such as those found in coal mines or manufacturing facilities, utilized a circuit configuration comprised of at least one sensing element. This sensing element was a wire having a catalytic coating. The sensing element was used as one of four legs of a wheatstone bridge circuit. The other three legs consisted of two resistors and a compensator element. The compensator element was identical to the sensing element except that it did not bear a catalytic coating.

A current or voltage was applied to the bridge circuit to heat the surface of the catalytic coating affixed to the sensing element. Since the resistance values of the other three legs of the bridge were known, the resistance in the sensing element could be determined as the current or voltage was passed through the bridge.

When the sensing element was exposed to a combustible gas, such as methane, the catalytic coating would begin to burn increasing the temperature of the sensing element. As the temperature of the sensing element increased, the resistance of the element increased. Accordingly, the current or voltage passing through the element decreased. By comparing the resistance level of the sensing element to the resistance level of the compensator element, the presence of a combustible gas could be detected. Since the amount of gas present caused a nearly linear increase or decrease in the resistance of the sensing element, the quantity of the gas could be accurately determined by calibrating the change in resistance. This is the basic principal of operation of a catalytic combustible gas sensor.

The actual use of this configuration does, however, possess drawbacks. For example, in the presence of high concentrations of combustible gases, the temperature rise of the catalytic coating can reach temperatures high enough to damage the sensing element. One method of alleviating this problem is to regulate the voltage or current that is passed through the sensing element. As heating causes the voltage or current to rise, a regulating circuit commonly known in the art, can be attached to the bridge to draw off some of the current or voltage. By reducing the current or voltage, harmful temperature extremes can be curtailed. The introduction of a regulating circuit can, however, introduce other errors that affect sensor performance. For example, regulating the voltage to the entire bridge circuit has relatively little effect on the sensor temperature. Also, another common practice, adjusting the bridge voltage to maintain a stable sensor voltage, is somewhat more effective, but does not stabilize the sensor sufficiently to prevent thermal damage.

Several combustible gas detectors that incorporate bridge circuits are known in the art. For example, Ferraro, U.S. Pat. No. 4,652,831, discloses a catalytic combustible gas detector that provides increased sensitivity to gases by pre-adjusting the voltage applied to the terminals of the sensing element. In this arrangement, the voltage must be pre-adjusted to the desired level dependent upon the type of gas to be tested. A second disclosure, Meyer E.P.C. Patent No. 018,221 provides an apparatus that incorporates two independent bridge circuits, one for the sensing element and one for the compensator element. The use of two circuits, however, requires twice the power consumption of a single bridge sensor. This can critically limit the portability of the instrument when the circuit is driven by batteries.

It is the intention of this invention to provide a combustible gas detecting circuit configuration that stabilizes the temperature of the sensing element to eliminate outside interference signals and thereby enable the circuit to provide faster response times, increased sensitivity and more accurate analyses of a gas in a manner that requires low power consumption while employing a single bridge circuit.

SUMMARY OF THE INVENTION

In accordance with the present invention, a new and improved catalytic combustible gas detector configuration is provided that overcomes the disadvantages of other prior art circuits. Specifically, the invention provides a bridge circuit where one of the four branches of the bridge is a sensing element and one of the other branches is a compensator element. A current or voltage is applied to the circuit and the individual resistances of the compensator element and the sensing element are determined. The elements are then exposed to a combustible gas and the new resistance of the sensing element is compared to the resistance of the compensating element. The difference in resistances is then amplified by means of a differential amplifier and sent to a current bypass device such as a transistor. When the difference signal is received by the transistor, the transistor becomes energized and draws off some of the electrical current from the sensing element. This brings the entire bridge circuit back into equilibrium and protects the sensing element from overheating. Even though current is drawn off of the sensing element, the sensing element is still able to change resistance with changes in the temperature of the sensor caused by its exposure to the gas stream. A signal indicating the concentration of combustible gas in the sample is then derived by measuring the current that is drawn by the transistor.

These features and other objectives of the invention will become apparent from the following detailed description taken in connection with the accompanying drawing.

BRIEF DESCRIPTION OF THE DRAWING

The drawing is a schematic circuit diagram of the gas detector having a temperature stabilization device.

DESCRIPTION OF THE PREFERRED EMBODIMENT

With reference to the drawing, a circuit diagram 100 of a combustible gas sensor is shown. A regulating device 101 provides either constant voltage or constant current to an electrical bridge circuit comprising a sensing element 102, a compensator element 103 and two resistors 104 and 105. The circuit 100 may be either a linear type or a switching type circuit and the regulating device 101 may be a voltage regulator or a current regulator. The preferred embodiment employs an integrated circuit switching voltage regulator. The regulating device 101 is used to independently control the overall power level in the sensing circuit 100. The circuit 100 should be powered at, for example, 3 volts or 0.140 amps. The sensing element 102 is a helix encapsulated to form a ceramic bead that is in turn impregnated with a noble metal catalyst, for example, paladium or platinum. The compensator element 103 is identical to the sensing element except that it does not bear a catalytic coating.

The sizes of the two resistors 104 and 105 are arbitrary. They could range from one ohm, that is wasteful of power, to 10 megohms, that is difficult to control. Since the ratio of these resistors is a known constant, the relative resistance of the sensing element 102 and compensator element 103 can be determined. Preferably the resistors 104 and 105 should be equal to provide for equal power in the elements 102 and 103. Since only the ratio of the resistors is important, the circuit is well suited to be built with hybrid or integrated circuit technology, in that, even though resistance values may be difficult to control in that type of circuit, the ratio of the resistances can be tightly controlled.

When the circuit is powered and the sensing element 102 is exposed to a combustible gas sample, the catalytic coating of the sensing element causes the combustible gas to burn and thereby raise the temperature of the sensing element 102. As the temperature increases, the resistance seen in the sensing element 102 increases. The voltage across the sensing element 102 increases proportionately according to the equation $V = IR$, where V is the voltage, I is the current and R is the resistance. When the current is held constant, the voltage increases linearly as the resistance increases.

The resistance in the compensator element 103 is affected by natural phenomenon such as humidity or heat as is the resistance of the sensing element 102, but since the compensation element 103 is not encased inside of a catalytic coating, its temperature is not affected by the presence of the combustible gas. Thus, the change in resistance in the sensing element 102 as compared to the resistance seen in compensator element 103 is caused solely by the burning of the combustible gas on the catalytic coating of the sensing element 102 when exposed to the combustible gas. The resistance change in the sensing element 102 caused by the temperature change, in turn, causes the voltage across the sensing element 102 to increase. The increase in voltage due to the presence of the combustible gas is determined by a difference amplifier 106. The difference amplifier 106 can be, for example, a single integrated circuit operational amplifier having performance characteristics of, for example, a gain of 10,000 or more, an input range of several volts and an input offset of less than 10 millivolts. Because of the nature of this circuit design the performance of the amplifier is not critical to the circuit and many commercially available devices are adequate.

The output signal of the amplifier 106 is connected to a bypass element 107. The bypass element 107 can be for example a transistor having performance characteristics of, for example, a breakdown voltage of several volts, a current rating of 1 ampere and a gain of 20 or more. When no combustible gas is present in the sample, there is no change in voltage across the sensing element 102 and hence no signal is generated by the difference amplifier 106. In this mode, the transistor 107 is turned off. When a combustible gas is present, and the difference amplifier 106 generates a signal that is applied to the base of the transistor 107, the transistor 107 turns on to draw off some of the electrical current from the sensing element 102 to bring the entire bridge circuit back into equilibrium. This stabilizes the temperature of the sensing element 102, thereby protecting the sensing element 102 from overheating when exposed to high concentrations of combustible gas. At the same time, the sensing element 102 continues to follow its normal tendency to change resistance with changes in the temperature of the sensing element 102, when exposed to combustible gases.

The concentration of combustible gas can be calculated by measuring the current emitted by the transistor 107 by means of a calibrated ammeter (not shown) or by measuring the voltage across a fixed resistor 108 in series with the bypass element. The calibration can be performed by measuring the current or voltage with the detector in an atmosphere absent of combustible gas. This arbitrary current, which may be zero, is equivalent to zero or no gas presence. The detector is then exposed to a gas of known concentration. The resulting current or voltage is equivalent to that known concentration. Other gas concentrations may be determined by interpolating or extrapolating from these values.

The invention has been described in its preferred embodiment. It is readily apparent that there are numerous modifications and variations of the present invention that may be made possible by the above teachings, while still remaining within the scope of the appended claims.

What is claimed is:

1. A catalytic gas detector circuit comprising:
   a bridge circuit having four branches and having input and output terminals wherein said input terminals are connected to a power source means capable of providing either constant current or constant voltage, and said output terminals are connected to a difference amplifier where;
   said first branch is a resistance gas sensing element having a catalytic coating that is reactive to combustible hydrocarbon gases;
   said second branch is a compensating element;
   said third and fourth branches are resistors;
   said difference amplifier output is connected to a current bypass means, that is parallel connected across said sensing element and responsive to said amplifier output, to pass current and; further having,
   a means to measure the current passed by said current bypass device.

2. The detector circuit according to claim 1 wherein said difference amplifier is an integrated circuit operational amplifier.

3. The detector circuit according to claim 1 wherein said bypass means is a transistor.

* * * * *